(12) United States Patent
Behnke, II et al.

(10) Patent No.: US 8,790,337 B2
(45) Date of Patent: Jul. 29, 2014

(54) SYSTEM AND METHOD FOR RETURN ELECTRODE MONITORING

(75) Inventors: Robert J. Behnke, II, Erie, CO (US); Robert H. Wham, Boulder, CO (US)

(73) Assignee: Covidien LP, Mansfield, MA (US)

( * ) Notice: Subject to any disclaimer, the term of this patent is extended or adjusted under 35 U.S.C. 154(b) by 33 days.

(21) Appl. No.: 13/480,644

(22) Filed: May 25, 2012

(65) Prior Publication Data

US 2012/0232548 A1  Sep. 13, 2012

Related U.S. Application Data

(63) Continuation of application No. 12/364,624, filed on Feb. 3, 2009, now Pat. No. 8,187,263.

(51) Int. Cl.
*A61B 18/04* (2006.01)

(52) U.S. Cl.
USPC .............................................. 606/35

(58) Field of Classification Search
USPC .................. 604/32–39, 22; 606/32–39
See application file for complete search history.

(56) References Cited

U.S. PATENT DOCUMENTS

| | | | |
|---|---|---|---|
| 4,094,320 A | 6/1978 | Newton et al. | |
| 4,416,276 A * | 11/1983 | Newton et al. | 606/35 |
| 4,416,277 A * | 11/1983 | Newton et al. | 606/35 |
| 4,657,015 A | 4/1987 | Irnich | |
| 4,658,819 A | 4/1987 | Harris et al. | |
| 4,699,146 A | 10/1987 | Sieverding | |
| 4,750,482 A | 6/1988 | Sieverding | |
| 4,844,063 A | 7/1989 | Clark | |
| 4,862,889 A | 9/1989 | Feucht | |
| 4,942,313 A | 7/1990 | Kinzel | |
| 5,061,914 A | 10/1991 | Busch et al. | |
| 5,196,008 A | 3/1993 | Kuenecke et al. | |
| 5,276,079 A | 1/1994 | Duan et al. | |
| 5,312,401 A | 5/1994 | Newton et al. | |
| 5,389,376 A | 2/1995 | Duan et al. | |
| 5,409,966 A | 4/1995 | Duan et al. | |
| 5,452,725 A | 9/1995 | Martenson | |
| 5,670,557 A | 9/1997 | Dietz et al. | |

(Continued)

FOREIGN PATENT DOCUMENTS

| | | |
|---|---|---|
| CA | 1219642 | 3/1987 |
| DE | 3206947 | 9/1983 |

(Continued)

OTHER PUBLICATIONS

U.S. Appl. No. 10/609,946, filed Jun. 30, 2003.

(Continued)

*Primary Examiner* — Manuel Mendez

(57) ABSTRACT

A return electrode monitoring ("REM") system is disclosed. The REM system includes a return electrode pad having a pair of split electrode pads and a detection circuit coupled to the pair of split electrode pads. The detection circuit and the pair of split electrode pads are adapted to resonate across a predetermined resonance range. The REM system also includes a controller coupled to the detection circuit and configured to provide a sweeping drive signal to the detection circuit across the resonance range. The detection circuit generates a drive signal in response to the sweeping drive signal and the controller determines a complex impedance across the at least one pair of split electrode pads as a function of the drive signal.

15 Claims, 3 Drawing Sheets

(56) References Cited

U.S. PATENT DOCUMENTS

| | | |
|---|---|---|
| 5,674,561 A | 10/1997 | Dietz et al. |
| 5,678,545 A | 10/1997 | Stratbucker |
| 5,688,269 A | 11/1997 | Newton et al. |
| 5,695,494 A | 12/1997 | Becker |
| 5,779,632 A | 7/1998 | Dietz et al. |
| 5,817,091 A | 10/1998 | Nardella et al. |
| 5,836,942 A | 11/1998 | Netherly et al. |
| 5,846,558 A | 12/1998 | Nielsen et al. |
| 5,853,750 A | 12/1998 | Dietz et al. |
| 5,952,398 A | 9/1999 | Dietz et al. |
| 5,985,990 A | 11/1999 | Kantner et al. |
| 6,007,532 A | 12/1999 | Netherly |
| 6,059,778 A | 5/2000 | Sherman |
| 6,063,075 A | 5/2000 | Mihori |
| 6,121,508 A | 9/2000 | Bischof et al. |
| 6,171,304 B1 | 1/2001 | Netherly et al. |
| 6,200,314 B1 | 3/2001 | Sherman |
| 6,232,366 B1 | 5/2001 | Wang et al. |
| 6,275,786 B1 | 8/2001 | Daners |
| 6,358,245 B1 | 3/2002 | Edwards et al. |
| 6,413,255 B1 | 7/2002 | Stern |
| 6,488,678 B2 | 12/2002 | Sherman |
| 6,546,270 B1 | 4/2003 | Goldin et al. |
| 6,569,160 B1 | 5/2003 | Goldin et al. |
| 6,860,881 B2 * | 3/2005 | Sturm et al. ............. 606/35 |
| 7,025,765 B2 | 4/2006 | Balbierz et al. |
| 7,160,293 B2 | 1/2007 | Sturm et al. |
| 7,169,145 B2 | 1/2007 | Isaacson et al. |
| 7,267,675 B2 | 9/2007 | Stern et al. |
| 8,187,263 B2 * | 5/2012 | Behnke et al. ............. 606/35 |
| 2003/0139741 A1 | 7/2003 | Goble et al. |
| 2006/0173250 A1 | 8/2006 | Nessler |
| 2007/0049916 A1 | 3/2007 | Isaacson et al. |
| 2007/0073284 A1 | 3/2007 | Sturm et al. |
| 2007/0161979 A1 | 7/2007 | McPherson |
| 2007/0222458 A1 | 9/2007 | Eisele |
| 2007/0244478 A1 | 10/2007 | Bahney |
| 2008/0281310 A1 | 11/2008 | Dunning et al. |
| 2008/0281311 A1 | 11/2008 | Dunning et al. |
| 2009/0209953 A1 | 8/2009 | Schoenman |
| 2009/0223041 A1 | 9/2009 | Garrison |
| 2009/0234352 A1 | 9/2009 | Behnke |
| 2009/0234353 A1 | 9/2009 | McPherson |
| 2010/0241023 A1 | 9/2010 | Gilbert |

FOREIGN PATENT DOCUMENTS

| | | |
|---|---|---|
| DE | 3544443 | 6/1987 |
| DE | 4238263 | 5/1993 |
| DE | 4231236 | 3/1994 |
| DE | 19717411 | 11/1998 |
| DE | 19801173 | 7/1999 |
| DE | 10328514 | 6/2003 |
| DE | 102004010940 | 9/2005 |
| EP | 0262888 | 4/1988 |
| EP | 390937 | 10/1990 |
| EP | 836868 | 4/1998 |
| EP | 0930048 | 7/1999 |
| EP | 1051949 | 11/2000 |
| EP | 1076350 | 2/2001 |
| EP | 1468653 | 10/2004 |
| EP | 1645236 | 4/2006 |
| EP | 1707151 | 10/2006 |
| EP | 1808144 | 7/2007 |
| EP | 1902684 | 3/2008 |
| FR | 2276027 | 6/1974 |
| FR | 2516782 | 5/1983 |
| GB | 2054382 | 2/1981 |
| GB | 2374532 | 10/2002 |
| WO | WO 96/19152 | 6/1996 |
| WO | WO 97/37719 | 10/1997 |
| WO | WO 99/09899 | 3/1999 |
| WO | WO 99/11187 | 3/1999 |
| WO | WO 00/53113 | 9/2000 |
| WO | WO 00/65993 | 11/2000 |
| WO | WO 2004/028385 | 4/2004 |
| WO | WO 20051087124 | 9/2005 |
| WO | WO 2005/115262 | 12/2005 |
| WO | 2007/067943 A2 | 6/2007 |
| WO | WO 2008/009385 | 1/2008 |

OTHER PUBLICATIONS

U.S. Appl. No. 11/900,190, filed Sep. 10, 2007.
U.S. Appl. No. 12/407,008, filed Mar. 19, 2009.
Boyles, Walt; "Instrumentation Reference Book", 2002; Butterworth-Heinemann ; 262-264.
International Search Report EP05002027.0 dated May 12, 2005.
International Search Report EP05021944.3 dated Jan. 25, 2006.
International Search Report EP06006961 dated Aug. 3, 2006.
International Search Report EP06006961.4 dated Oct. 5, 2007.
International Search Report EP06018206.0 dated Oct. 13, 2006.
International Search Report EP06023756.7 dated Feb. 21, 2008.
International Search Report EP07000567.3 dated Dec. 3, 2008.
International Search Report EP07000885.9 dated May 15, 2007.
International Search Report EP07007783.9 dated Aug. 6, 2007.
International Search Report EP07018375.1 dated Jan. 8, 2008.
International Search Report EP07019173.9 dated Feb. 12, 2008.
International Search Report EP07019178.8 dated Feb. 12, 2008.
International Search Report EP07253835.8 dated Feb. 20, 2007.
International Search Report EP08006731.7 dated Jul. 29, 2008.
International Search Report EP08006734.1 dated Aug. 18, 2008.
International Search Report EP08006735.8 dated Jan. 8, 2009.
International Search Report EP08008510.3 dated Oct. 27, 2008.
International Search Report EP08013758.1 dated Nov. 20, 2008.
International Search Report EP08013760.7 dated Nov. 20, 2008.
International Search Report EP08155779—partial dated Sep. 8, 2008.
International Search Report EP08155779 dated Jan. 23, 2009.
International Search Report EP09152032 dated Jun. 17, 2009.
International Search Report EP09152130.2 dated Apr. 6, 2009.
International Search Report PCT/US2004/004196 dated Oct. 4, 2007.
EP Examination Report from Appl. No. 09152032.0 dated Feb. 12, 2013.
Australian Examination Report from Appl. No. 2009200404 dated Mar. 22, 2013.
JP Official Action issued in Appl. No. 2009-023772 dated May 9, 2013.

* cited by examiner

SYSTEM AND METHOD FOR RETURN ELECTRODE MONITORING

CROSS-REFERENCE TO RELATED APPLICATION

The present application is a continuation application of U.S. patent application Ser. No. 12/364,624, filed on Feb. 3, 2009, the entire contents of which are incorporated by reference herein.

BACKGROUND

1. Technical Field

The present disclosure relates to electrosurgical apparatuses, systems and methods. More particularly, the present disclosure is directed to electrosurgical systems configured to monitor contact quality of return electrode pads to the patient during electrosurgical procedures.

2. Background of Related Art

Energy-based tissue treatment is well known in the art. Various types of energy (e.g., electrical, ultrasonic, microwave, cryogenic, heat, laser, etc.) are applied to tissue to achieve a desired result. Electrosurgery involves application of high radio frequency electrical current to a surgical site to cut, ablate, coagulate or seal tissue. In monopolar electrosurgery, the active electrode is typically part of the surgical instrument held by the surgeon and applied to the tissue to be treated. A patient return electrode is placed remotely from the active electrode to carry the current back to the generator and safely disperse current applied by the active electrode.

The return electrodes usually have a large patient contact surface area to minimize heating at that site. Heating is caused by high current densities which directly depend on the surface area. A larger surface contact area results in lower localized heat intensity. Return electrodes are typically sized based on assumptions of the maximum current utilized during a particular surgical procedure and the duty cycle (i.e., the percentage of time the generator is on).

The first types of return electrodes were in the form of large metal plates covered with conductive jelly. Later, adhesive electrodes were developed with a single metal foil covered with conductive jelly or conductive adhesive. However, one problem with these adhesive electrodes was that if a portion peeled from the patient, the contact area of the electrode with the patient decreased, thereby increasing the current density at the adhered portion and, in turn, increasing the heating at the tissue. This risked burning the patient in the area under the adhered portion of the return electrode if the tissue was heated beyond the point where circulation of blood could cool the skin.

To address this problem various return electrodes and hardware circuits, generically called Return Electrode Contact Quality Monitors (RECQMs), were developed. Such systems relied on measuring impedance at the return electrode to calculate a variety of tissue and/or electrode properties. These systems detected peeling by identifying changes in amplitude of the impedance of the return electrodes.

SUMMARY

The present disclosure relates to a return electrode monitoring system which measures a voltage, current and phase with respect to frequency of an interrogation waveform. The system also sweeps the frequency of the interrogation waveform thereof to obtain the measurements and track the frequency response of the return electrode monitoring circuit to determine a complex impedance.

According to one aspect of the present disclosure a return electrode monitoring ("REM") system is disclosed. The REM system includes a return electrode pad having one or more pairs of split electrode pads and a detection circuit coupled to the pair of split electrode pads. The detection circuit and the pair of split electrode pads are adapted to resonate across at a predetermined resonance. The REM system also includes a controller coupled to the detection circuit and configured to provide a sweeping drive signal to the detection circuit across the resonance range. The controller determines a complex impedance across the at least one pair of split electrode pads as a function of the drive signal.

A method for monitoring a return electrode is also contemplated by the present disclosure. The method includes the steps of providing a drive signal to a return electrode monitoring system including a return electrode pad having one or more pairs of split electrode pads. The return electrode monitoring system is adapted to resonate at predetermined resonance. The method also includes the steps of sweeping the drive signal across the predetermined resonance range, generating a drive signal in response to the sweeping drive signal, measuring the phase of the drive signal and determining a complex impedance across the return electrode monitoring system as a function of the phase of the drive signal.

According to another aspect of the present disclosure an electrosurgical system is provided. The system includes a return electrode monitoring system adapted to resonate at a predetermined resonance. The return electrode monitoring system includes a return electrode pad having one or more pairs of split electrode pads and a detection circuit coupled to the pair of split electrode pads. The system also includes a controller coupled to the return electrode monitoring system and configured to provide a sweeping drive signal to the return electrode monitoring system across the resonance range thereof. The detection circuit then measures a voltage, current and phase with respect to frequency of a corresponding drive signal of the drive signal. The controller determines a complex impedance across the pair of split electrode pads as a function of the voltage, current and phase of the drive signal.

According to a further aspect of the present disclosure, a return electrode monitoring ("REM") system is disclosed. The REM system includes a return electrode pad having one or more pairs of split electrode pads and a detection circuit coupled to the pair of split electrode pads. The detection circuit and the pair of split electrode pads are adapted to resonate across at a predetermined resonance. The REM system also includes a controller coupled to the detection circuit and configured to provide one of a step signal or an impulse signal to the detection circuit. The detection circuit is adapted to measure a signal response to at least one of the step and the impulse signal and convert the signal response to a frequency response, the controller being further configured to determine a complex impedance across the pair of split electrode pads as a function of the frequency response.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

Return electrode monitoring ("REM") circuitry in an electrosurgical generator monitors contact area between the patient and one or more return electrode pads. The circuitry prevents tissue damage caused by pad burns due to poor pad contact. The REM circuitry forms a resonant system with the split electrode pads of the return electrode pads which are designed to resonate at a specific interrogation frequency. The REM circuitry detects a signal in response to a supplied drive signal at a predetermined clock frequency (e.g., from a controller). The REM circuitry thereafter produces a voltage indicative of the amplitude (e.g., magnitude) of the waveform indicative of the resonations. As the impedance between the split pads changes, the resonance of the REM circuit changes as well, this causes the amplitude to change. Thus, by monitoring the changes in the amplitude, the REM circuit determines the magnitude of the impedance between the split pads which is indicative of adherence of the return electrode pad to the patient.

The present disclosure provides for an REM circuit which measures not only the magnitude of the impedance but also voltage, current and phase with respect to frequency of the waveform. This allows the REM circuit to measure any shift in frequency along with the amplitude shift. The shift in frequency is indicative of a shift in reactance across the REM circuit. Reactance provides a more detailed measurement of the adherence of the return electrode pad to the patient. More specifically, as the return electrode pad is placed on the patient, the reactance thereof (e.g., capacitance) changes the resonance frequency of the REM circuit. Thus, any detected changes to the reactance directly relate to the overall adherence factor of the return electrode pad.

Figure 1:
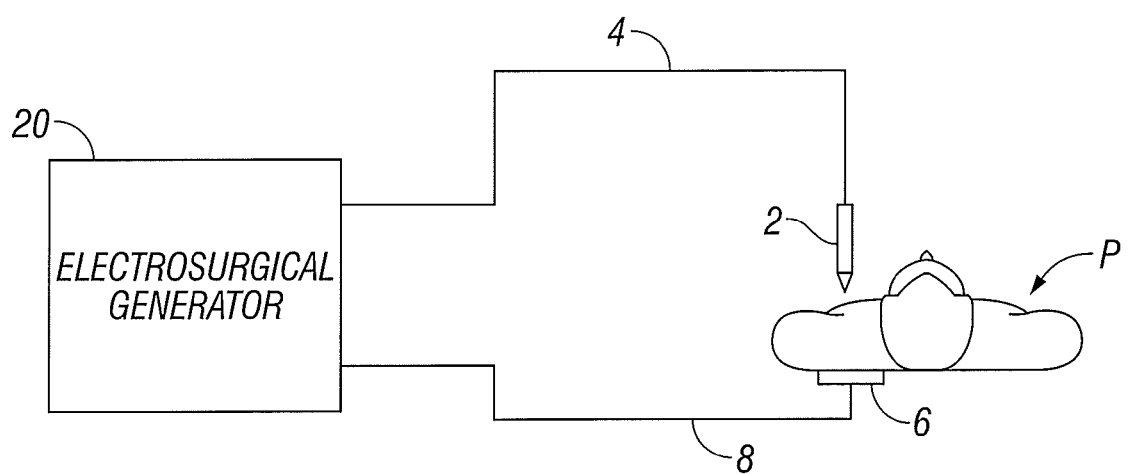
FIG. 1 is a schematic block diagram of an electrosurgical system according to the present disclosure.

FIG. 1 is a schematic illustration of an electrosurgical system according to one embodiment of the present disclosure. The system includes an electrosurgical instrument 2 having one or more electrodes for treating tissue of a patient P. The instrument 2 is a monopolar instrument including one or more active electrodes (e.g., electrosurgical cutting probe, ablation electrode(s), etc.). Electrosurgical RF energy is supplied to the instrument 2 by a generator 20 via an electrosurgical cable 4, which is connected to an active output terminal, allowing the instrument 2 to coagulate, ablate and/or otherwise treat tissue. The energy is returned to the generator 20 through a return electrode pad 6 via a return cable 8. The system may include a plurality of return electrodes pads 6 that are arranged to minimize the chances of tissue damage by maximizing the overall contact area with the patient P. In addition, the generator 20 and the return electrode 6 may be configured for monitoring so-called "tissue-to-patient" contact to insure that sufficient contact exists therebetween to further minimize chances of tissue damage.

The generator 20 includes input controls (e.g., buttons, activators, switches, touch screen, etc.) for controlling the generator 20. In addition, the generator 20 may include one or more display screens for providing the user with variety of output information (e.g., intensity settings, treatment complete indicators, etc.). The controls allow the user to adjust power of the RF energy, waveform, and other parameters to achieve the desired waveform suitable for a particular task (e.g., coagulating, cauterizing, intensity setting, etc.). The instrument 2 may also include a plurality of input controls that may be redundant with certain input controls of the generator 20. Placing the input controls at the instrument 2 allows for easier and faster modification of RF energy parameters during the surgical procedure without requiring interaction with the generator 20.

Figure 2:
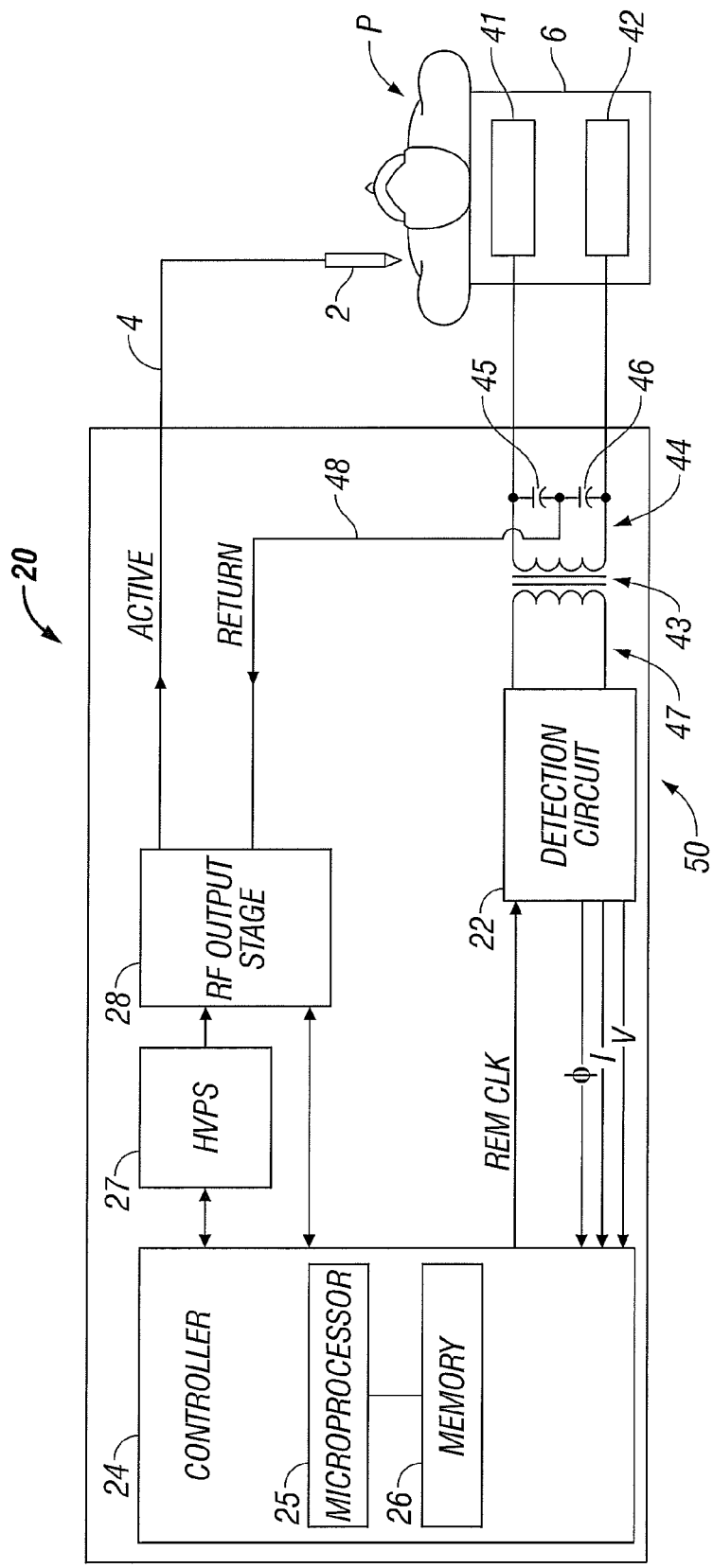
FIG. 2 is a schematic block diagram of a generator according to one embodiment of the present disclosure.

FIG. 2 shows a schematic block diagram of the generator 20 having a controller 24, a high voltage DC power supply 27 ("HVPS") and an RF output stage 28. The HVPS 27 provides high voltage DC power to an RF output stage 28, which then converts high voltage DC power into RF energy and delivers the RF energy to the active electrode. In particular, the RF output stage 28 generates sinusoidal waveforms of high RF energy. The RF output stage 28 is configured to generate a plurality of waveforms having various duty cycles, peak voltages, crest factors, and other suitable parameters. Certain types of waveforms are suitable for specific electrosurgical modes. For instance, the RF output stage 28 generates a 100% duty cycle sinusoidal waveform in cut mode, which is best suited for ablating, fusing and dissecting tissue, and a 1-25% duty cycle waveform in coagulation mode, which is best used for cauterizing tissue to stop bleeding.

The controller 24 includes a microprocessor 25 operably connected to a memory 26, which may be volatile type memory (e.g., RAM) and/or non-volatile type memory (e.g., flash media, disk media, etc.). The microprocessor 25 includes an output port that is operably connected to the HVPS 27 and/or RF output stage 28 that allows the microprocessor 25 to control the output of the generator 20 according to either open and/or closed control loop schemes. Those skilled in the art will appreciate that the microprocessor 25 may be substituted by any logic processor (e.g., control circuit) adapted to perform the calculations discussed herein.

The generator 20 includes a return electrode monitoring ("REM") system 50 having a detection circuit 22 which is coupled to a pair of split electrode pads, a first electrode pad 41 and a second electrode pad 42 disposed within the return electrode pad 6. The return electrode pad 6 is in contact with the patient P and returns the electrosurgical energy to the generator 20 via the first and second electrode pads 41 and 42 that are coupled to leads 51 and 52, respectively. In one embodiment, the return electrode pad 6 may include a plurality of pairs of split electrode pads which are coupled to a corresponding number of leads. The leads 51 and 52 are enclosed in a return cable 8 and are terminated at a secondary winding 44 of a transformer 43. The leads 51 and 52 are interconnected by capacitors 45 and 46. A return lead 48 is coupled between the capacitors 44 and 46 and is adapted to return the electrosurgical energy to the RF output stage 28. The transformer 43 of the REM system 50 also includes a primary winding which is connected to the detection circuit 22. The REM system 50 also includes a voltage sensor 54 and a current sensor 53 disposed on a primary side of the transformer 43.

Components of the REM system 50, e.g., the transformer 43, the split pads 41 and 42, the capacitors 44 and 46 along with the detection circuit 22 form a resonant system which is adapted to resonate at a specific interrogation frequency from the controller 24. Namely, the controller 24 provides a drive signal, REM CLK, at the specific interrogation frequency to the detection circuit 22. The drive signal, REM CLK, is a clock signal generated by the controller 24 at the desired frequency. The drive signal is a constant, physiologically benign waveform (e.g., 140 kHz, 2 mA) which the detection circuit 22 applies to the first electrode pad 41. The drive signal thereafter passes through the patient and is returned to the circuit 22 via the second electrode pad 42. The detection circuit 22 then measures a response signal to the drive signal and monitors the changes in the response signal.

The response signal (e.g., returning drive signal) is modified by the impedance of the first and second electrode pads 41 and 42. More specifically, as the impedance between the split electrode pads 41 and 42 changes due to peeling of the return electrode pad 6 from the patient, the resonance of the detection circuit 22 with respect to other components changes as well. The change in the resonance, in turn, affects the change in amplitude of the drive signal. Thus, the detection circuit 22 determines the magnitude of the impedance between the first and second electrode pads 41 and 42 by monitoring changes in amplitude of the drive signal. The detection circuit 22 then supplies the impedance measurement to the controller 24 which determines whether the impedance is within a predetermined range. If the impedance is out of range, which denotes excessive peeling of the return electrode pad 6, the controller 24 issues an alarm and/or adjusts the output of the generator 20 (e.g., terminates RF energy supply).

The above-described operation of the detection circuit 22 using a single frequency REM CLK signal only allows for measuring a relative change in the magnitude of the impedance. In other words, regardless of the load, the relative change in the drive signal due to the adherence of the electrosurgical return pad 6 stays the same. Thus, the detection circuit 22 when operating on a single frequency drive signal can only determine the change in amplitude and not any other characteristics of the adherence of the electrosurgical return pad 6.

In another embodiment, the detection circuit 22 tracks the frequency response of the REM system 50 and determines the complex impedance thereacross. Electrical impedance describes not only the relative magnitudes of the voltage and current, but also the relative phases. Impedance is a so-called "complex" value wherein the "real" part relates to the resistance and the "imaginary" part relates to the reactance. The above-described embodiment provides for measuring only the magnitude of the impedance. In other words, the detection circuit 22 measures the resistance component of the impedance which then serves as an estimate of the actual impedance. In order to measure the actual impedance, both the resistance and the reactance components (e.g., real and imaginary components) must be measured and calculated. The present disclosure provides for an REM system 50 and method for determining actual complex impedance.

The REM system 50 forms a resonant system which is adapted to resonate at a specific interrogation frequency from the controller 24. The controller 24 is configured to sweep the drive signal, REM CLK, across a resonance range in order to determine a frequency response, which is then used to determine complex impedance of the return electrode pad 6. Namely, the controller 24 provides a plurality of drive signals, REM CLK, across the resonance range in predetermined frequency increments.

The drive signal, REM CLK, may be either a square wave, a sine wave, an impulse or step signal. If the drive signal is either an impulse or a step signal, in addition to the processing steps outlined below for the square and sine wave drive signals, the frequency response is also determined by using any type of waveform processing such as fast Fourier transform, Goertzel algorithm, any combination thereof, and the like.

If the drive signal is either a sine or a square wave, the frequency of the drive signal is swept from a first predetermined frequency (e.g., $f_a$) to a second predetermined frequency (e.g., $f_b$) across the resonance range. The drive signal passes through the patient and is returned to the detection circuit 22 via the second electrode pad 42. In addition to measuring the amplitude of the drive signal to obtain the magnitude of the impedance, the detection circuit 22 also measures voltage, current and phase thereof with respect to frequency. More specifically, for each frequency, the voltage sensor 54 measures the voltage and the current sensor 53 measures the current. The measured voltage and current are then transmitted to the controller 24 which determines a phase difference between the measured voltage and current outputs. The controller 24 calculates the phase for both the voltage and current of the REM CLK signals as measured by the detection circuit 22. The controller 24 also calculates the phase difference between the measured output voltage and current. In one embodiment, the detection circuit 22 may also be adapted to determine the phase difference directly. The phase difference between the output voltage and current is substantially the same as the difference between the output current and the drive signal, REM CLK. Therefore, measuring the phase difference between the output voltage and current allows for a determination of the phase difference between the drive signal and the output current.

The controller 24 then determines the frequency response at each frequency between $f_a$ and $f_b$ by calculating the magnitude of output voltage, output current and the phase difference.

Using the frequency response, the complex impedance of the return electrode pad 6 may be determined once other variables are known.

To determine the "imaginary" portion of the complex impedance, the return electrode pad 6 may be modeled as a parallel plate capacitor when adhered to patient tissue (e.g., skin). The tissue, or the surface of the tissue in contact with the return electrode pad 6 has a predetermined dielectric constant, $\epsilon_r$. The capacitance of the tissue-return electrode pad model, $C_{pat}$, may be expressed by the following formula (I):

$$C_{pat}=(\epsilon_r * A)/d \tag{I}$$

In the formula (I), A is a surface area of the return electrode pad 6 that is in contact with the tissue and d is the distance between the split pads 41 and 42. Thus, the surface area, A, is representative of the adherence of the return electrode pad 6 to the tissue.

The present disclosure allows for determination of the surface area, A, and thus, the adherence of the return electrode pad 6 by determining the capacitance of the return electrode pad 6 based on the frequency response of the REM system 50. More specifically, the capacitance $C_{pat}$ of formula (I) may be measured once the shift in the resonance frequency is known based on the following formula (II):

$$2\pi * f_{res} = 1/\sqrt{(L_1 * (C_1 * C_{pat})/(C_{pat}+C_1))} \tag{II}$$

In the formula (II), $f_{res}$ is the resonance frequency determined based on the frequency response to the drive signal, REM CLK, $L_1$ and $C_1$ are known inductance and capacitance of the REM system 50 (e.g., capacitors 45 and 46).

The change in magnitude of the measured impedance is used to determine the "real" portion of the complex impedance. More specifically, a comparison between a first $f_{res}$, which corresponds to the resonant frequency of REM system 50 when the return electrode pad 6 is disconnected and a second $f_{res}$, which corresponds to the return electrode pad 6 being connected to the REM system 50 and in contact with a patient, allows for a determination of the real portion of the complex impedance. The difference between the first and second resonant frequencies is caused by electrical resistance between the split pads 41 and 42 of the return electrode pad 6. Once the real and imaginary portions of the impedance of the return electrode pad 6 are known, these values may be used to determine the surface area of the return electrode pad 6 in contact with the patient. During operation, the controller 24 tracks the changes in complex impedance and correlates those changes with the adherence factor of the return electrode pad 6. Thus, the controller 24 determines whether the return electrode pad 6 is attached or is in the process of peeling.

The controller 24 utilizes the shift in amplitude of the drive signal to determine series resistance between the return electrode pad 6 and the patient. Since the controller 24 can calculate the resistance (e.g., from the amplitude shift) and the reactance (e.g., from the frequency shift), the controller 24 also determines the complex impedance. This allows for the determination of the total amount of energy which can safely pass through the return electrode pad 6. The REM system 50 also tracks any drift relating to the total energy, temperature changes, material properties and once detected, an alarm may be issued by the controller 24 or an adjustment to the output may be made.

In one embodiment, varying or sweeping the frequency to determine the frequency response of the REM system 50 may also be accomplished via impulse response or step response interrogation schemes. More specifically, a step or narrow pulse input may also be sent to the REM system 50 and the resulting responses captured and monitored by the detection circuit 22. The response (e.g., drive signal) to a pulse is called an impulse response, performing a fast Fourier transform or another type of signal analysis on this response signal provides the frequency response of the REM system 50 which can be used as specified above for both amplitude and phase responses. The response to a step (e.g., drive signal) is called a step response, and the derivative of the step response is the impulse response which can be converted to the frequency response which is within the purview of those skilled in the art. Either of these methods may also be used to model an equivalent circuit and thus determine the complex impedance between the return electrode pad 6 and the patient.

Figure 3:
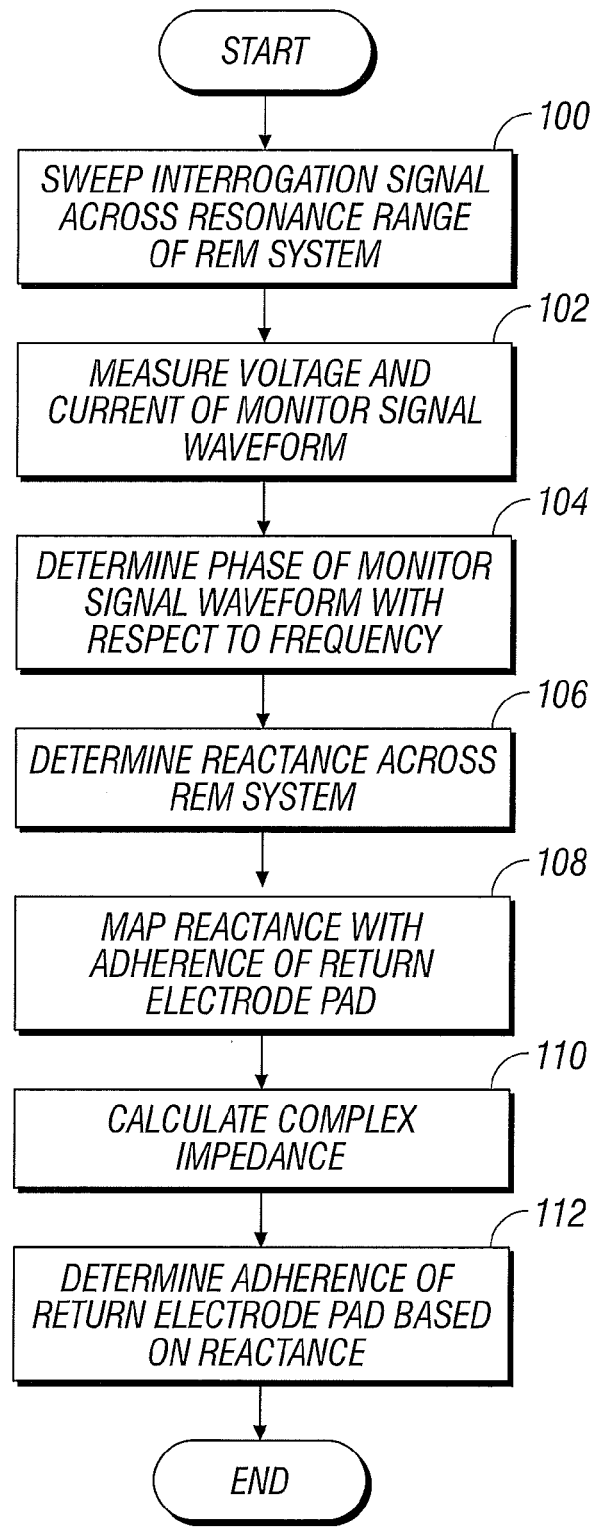
FIG. 3 is a flow chart illustrating a method according to the present disclosure.

A method for determining complex impedance across the REM system 50 is also disclosed herein and is by example shown in FIG. 3. In step 100, the controller 24 sweeps the drive signal, REM CLK, across the resonance range of the REM system 50. In step 102, the detection circuit 22 measures the output current and voltage response of the drive signal, which in step 104, are used by the controller 24 to determine the phase of the drive signal with respect to frequency. The controller 24 also determines the resistance component of the impedance based on the amplitude of the voltage response. In step 106, the controller 24 determines the reactance as a function of the voltage, current and phase values with respect to frequency and the resistance based on the amplitude of the waveform. The controller 24 also determines the resistance based on the drop in resonant frequency as discussed above. In one embodiment, the frequency response of the REM system 50 may be used to determine the complex impedance thereof, in response to which the controller 24 may perform desired operations (e.g., alarm, output adjustment, etc.). In step 108, the resistance and the reactance components are used to calculate the complex impedance across the REM system 50. The controller 24 thereafter determines in step 112 the relative adherence of the return electrode pad 6 and the amount of energy flowing through the return electrode pad 6.

According to another embodiment of the present disclosure, the type of the return electrode pad 6 being used may also be determined by measuring the surface area thereof using the complex impedance. Various types of return electrode pads 6 are used based on the type of procedure and/or patient size (e.g., pediatric, full size, ablation, etc.). By determining the area of the return electrode pad 6, the controller 24 may then automatically determine the type of the return electrode pad 6 and adjust the operating parameters of the generator 20 accordingly.

The area of the return electrode pad 6 is determined by first calculating the capacitance of the tissue-return electrode pad model, $C_{pat}$, and then calculating the area as a function of the capacitance. The calculation of the area may be performed at the start of the procedure since the return electrode pad 6 is fully adhered to the patient at that time. Once the area of the pad is determined, the controller 24 may then access a lookup table or another data structure as stored in the memory 26 to determine the type of the return electrode pad 6. The controller 24 then calculates, based on the type of pad 6, a safe amount of current and energy application time limits to maintain the tissue under the return electrode pad 6 from heating to undesired levels. In addition, the controller 24 may also adjust maximum energy output and other output parameters (e.g., duty cycle) to keep the tissue heating within desired limits. In another embodiment, the controller 24 may limit user-selectable modes of operation of the generator 20 based on the type of the return electrode pad 6. The limits imposed by the controller 24 may also be adjusted in real-time during the procedures, so that as the surface area or impedance of the return electrode pad 6 changes during the procedure, the allowed output and duty cycle are modified.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A return electrode monitoring system comprising:
   at least one return electrode pad including at least one pair of split electrode pads;
   a detection circuit operatively coupled to the at least one pair of split electrode pads; and
   a controller coupled to the detection circuit and configured to provide a drive signal to the detection circuit, wherein the detection circuit is adapted to measure a response signal in response to the drive signal and convert the response signal to a frequency response, the controller being further configured to determine a phase of the drive signal with respect to a frequency of the response signal, a complex impedance across the at least one pair of split electrode pads as a function of the frequency response, and a frequency shift as a function of the phase of the drive signal.

2. The return electrode monitoring system according to claim 1, wherein the detection circuit is configured to measure a voltage, a current and a phase difference therebetween of the drive signal.

3. The return electrode monitoring system according to claim 1, wherein the controller is configured to determine a reactance across the at least one pair of split electrode pads.

4. The return electrode monitoring system according to claim 3, wherein the controller is configured to determine a resistance across the at least one pair of split electrode pads as a function of a change in amplitude of the voltage of the drive signal.

5. The return electrode monitoring system according to claim 4, wherein the controller is configured to determine a complex impedance across the at least one pair of split electrode pads as a function of the resistance and the reactance.

6. The return electrode monitoring system according to claim 1, wherein the drive signal is at least one of a step or an impulse signal.

7. A method for monitoring a return electrode comprising:
provide a drive signal to a return electrode monitoring system including at least one return electrode pad having at least one pair of split electrode pads, the return electrode monitoring system being adapted to resonate across a predetermined resonance;
sweeping the drive signal across a resonance range of the predetermined resonance;
generating a response signal in response to the sweeping of the drive signal;
converting the response signal to a frequency response;
determining a complex impedance across the at least one pair of split electrode pads as a function of the frequency response; and
determining a resistance across the at least one pair of split electrode pads as a function of a change in amplitude of the drive signal.

8. The method for monitoring a return electrode according to claim 7, further comprising:
measuring a voltage and a current of the drive signal.

9. The method for monitoring a return electrode according to claim 8, further comprising:
measuring a phase of the drive signal; and
determining complex impedance across the at least one pair of split electrode pads as a function of the phase of the drive signal.

10. The method for monitoring a return electrode according to claim 7, further comprising:
determining a phase of the drive signal with respect to a frequency of the response signal.

11. The method for monitoring a return electrode according to claim 10, further comprising:
determining a frequency shift as a function of the phase of the drive signal.

12. The method for monitoring a return electrode according to claim 7, further comprising:
determining a complex impedance across the at least one pair of split electrode pads as a function of the resistance and the reactance.

13. The method for monitoring a return electrode according to claim 7, further comprising:
determining a reactance across the at least one pair of split electrode pads.

14. The method for monitoring a return electrode according to claim 13, further comprising:
mapping the reactance across the at least one pair of split electrode pads with adherence of the at least one return electrode pad.

15. The method for monitoring a return electrode according to claim 7, wherein the drive signal is at least one of a step or an impulse signal.

* * * * *